United States Patent [19]
Fournet-Fayard et al.

[11] Patent Number: 5,584,833
[45] Date of Patent: Dec. 17, 1996

[54] DEVICE FOR RETAINING A CONNECTING ROD OF A SPINE FIXATOR ON A PEDICULAR SCREW

[75] Inventors: Jacques Fournet-Fayard, Valence; Christophe Garin, Lyons; Olivier Galland, Meylan; Alain Lucet, Dijon, all of France

[73] Assignee: Soprane S.A., Lyons, France

[21] Appl. No.: 428,311

[22] Filed: Apr. 25, 1995

[30] Foreign Application Priority Data

Apr. 25, 1994 [FR] France ................................. 94 05189

[51] Int. Cl.⁶ .................................................. A61B 17/56
[52] U.S. Cl. ............................................... 606/61; 606/60
[58] Field of Search ............................ 606/60, 61, 69, 606/72, 73, 54, 59; 403/302, 373, 388, 394; 24/297, 324, 662

[56] References Cited

U.S. PATENT DOCUMENTS 4,579,473  4/1986  Brugger ................................. 403/163
5,380,323  1/1995  Howland ................................. 606/61

Primary Examiner—Michael Powell Buiz
Assistant Examiner—Mark S. Leonardo
Attorney, Agent, or Firm—Dowell & Dowell

[57] ABSTRACT

This invention relates to a device for retaining a connecting rod of a spine fixator on a pedicular screw, wherein it comprises two identical ring-shaped elements, of which each comprises an opening bore of conical profile, at least one cylindrical notch made perpendicularly to the conical bore for positioning a connecting rod, at least one elastically deformable finger and at least one vertical hole which is intended to receive and maintain the corresponding finger of the other ring before assembly thereof on the corresponding pedicular screw.

14 Claims, 2 Drawing Sheets

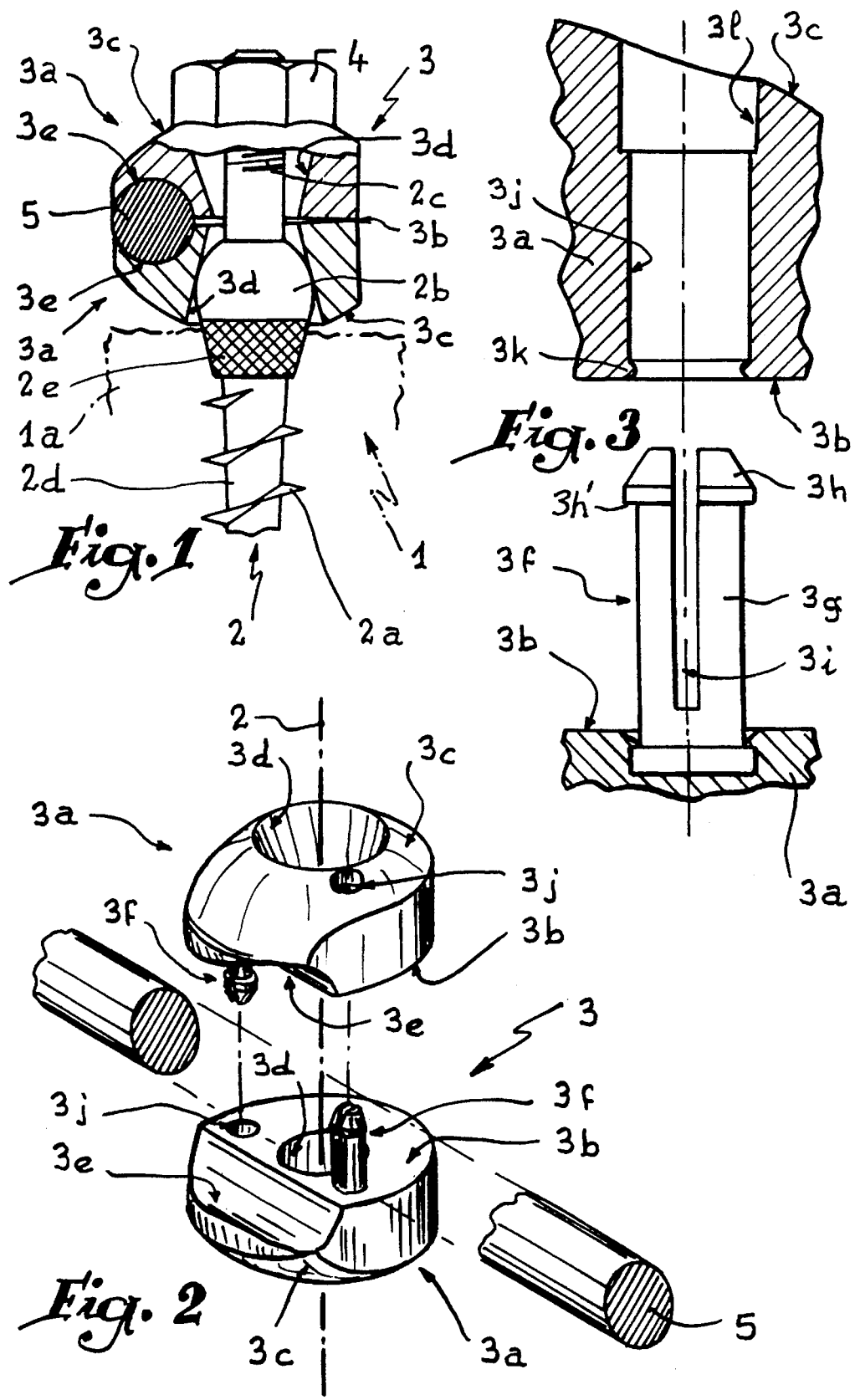

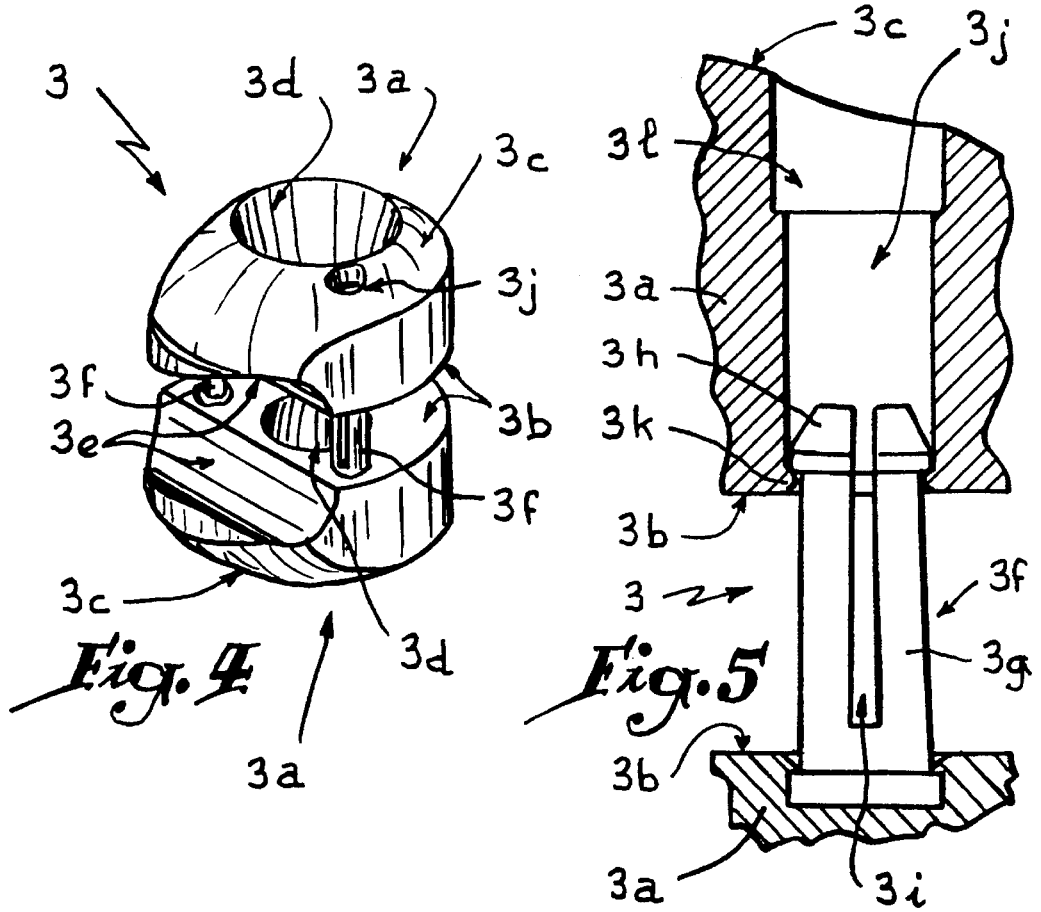
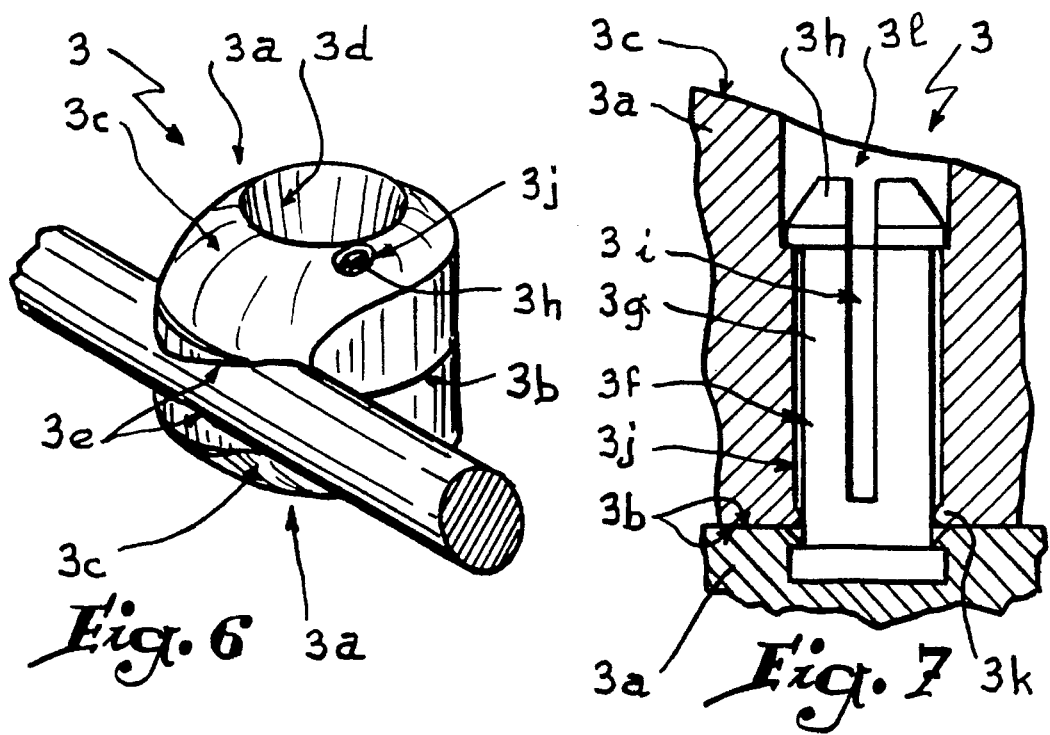

DEVICE FOR RETAINING A CONNECTING ROD OF A SPINE FIXATOR ON A PEDICULAR SCREW

BACKGROUND OF THE INVENTION

1. Field of the Invention

The present invention relates to a device for retaining a connecting rod of a spine fixator on pedicular screws previously anchored in the pedicles of the lumbar vertebrae of a backbone.

2. History of the Related Art

Several types of devices for retaining the connecting rods of spine fixators are known.

Retaining devices exist, which are mounted on the connecting rod before it is positioned on the pedicular screws anchored in the lumbar vertebrae. These devices are constituted by rings having an internal profile identical to that of the rod in order to be traversed thereby. Nuts enable the rod to be secured inside the rings. These retaining devices require perfect alignment of the pedicular screws in the sagittal and frontal plane. In fact, if the alignment is not proper, connection with the rod is impossible unless the latter is deformed to recover the angular shift. Deformation of the rod does not facilitate slidable adjustment and positioning of the retaining devices before fixation of the rod on the pedicular screws.

Other retaining devices are mounted as and when needed on the pedicular screws anchored in the pedicles of the lumbar vertebrae. These devices require considerable dexterity of the surgeon to assemble all the elements of the spine fixator on the pedicular screws.

None of the retaining devices described heretofore enables surgeons to choose the manner of assembling the fixator on the pedicular screws, i.e. either positioning the connecting rod secured to the retaining devices, or assembling as the operation is being carried out.

It is a particular object of the present invention to overcome these drawbacks.

The purpose of the retaining devices according to the invention is to allow surgeons to choose the best adapted assembly of the fixator on the pedicular screws depending on the surgical difficulties encountered.

SUMMARY OF THE INVENTION

The retaining device according to the invention comprises two identical ring-shaped elements each comprising elastically deformable retaining means which enable the rings to be maintained with respect to one another in different positions before their final assembly on a corresponding pedicular screw.

The retaining device comprises two identical ring-shaped elements, of which each comprises an opening bore of conical profile, at least one cylindrical notch made perpendicularly to the conical bore for positioning and guiding a connecting rod, at least one elastically deformable finger and at least one vertical hole which is intended to receive and retain the corresponding finger of the other ring.

BRIEF DESCRIPTION OF THE DRAWINGS

The invention will be more readily understood on reading the following description with reference to the accompanying drawings, in which:

FIG. 1 is a view showing a pedicle of a lumbar vertebra in which is fixed a pedicular screw to which the retaining device according to the present invention is mounted.

FIG. 2 is an exploded view in perspective illustrating the ring-shaped elements constituting the retaining device according to the present invention.

FIG. 3 illustrates in section the connecting device between the ring elements prior to assembly thereof.

FIGS. 4 and 5 are views showing the first position of use of the retaining device.

FIGS. 6 and 7 are views similar to those of FIGS. 4 and 5, but illustrating the second position of use of the device.

DESCRIPTION OF PREFERRED EMBODIMENT

Referring now to the drawings, FIG. 1 shows the pedicle 1a of a lumbar vertebra 1 of the lower part of a spine in which is fixed a pedicular screw 2. The pedicular screw 2 receives in its upper part a retaining device 3 which, via a nut 4, allows a connecting rod 5 to be tightened.

The spine fixator is composed of a plurality of identical elements, as shown in FIG. 1, which are immobilized on the pedicles 1a of each damaged vertebra 1 so as to dispose two connecting rods 5 parallel to the spines of vertebrae (processi spinosi).

The pedicular screw 2 comprises a thread 2a and a spherical head 2b of which the upper part is secured to a threaded rod 2c coaxial to the thread 2a.

The thread 2a comprises a core 2d of conical profile so as to ensure a better stability of the upper part of the screw 2. The wider base of the conical profile of the core 2d is provided towards the spherical head 2b of the pedicular screw 2.

The spherical head 2b extends on the thread 2a side in a conical part 2e having a rough surface to allow progressive and long-lasting biological anchoring for the bone around the head.

The threaded head 2c is provided to be of variable length depending on the point of anchoring of the pedicular screw 2. Moreover, the threaded rod 2c may be provided to be divisible as a function of the height used.

FIG. 2 shows the retaining device 3 which is constituted by two identical ring-shaped clamping elements 3a which may reciprocally form either the lower part or the upper part of the retaining device. Each ring clamping element 3a presents a plane bearing surface 3b and a spherical outer profile 3c. Each ring 3a is provided with an opening bore 3d which is offset laterally with respect to the vertical axis of the rings. The bore 3d has a conical profile whose wider base is turned towards the spherical profile 3c of the rings 3a.

Near the bearing surface 3b and at right angles to the axis of the conical bore 3d there ms provided a connecting rod engaging surface or notch 3e of partially cylindrical section which is oriented toward and opens out on face 3b.

An elastically deformable retaining element or finger 3f is fixed on each of the rings 3a of the device 3. The finger 3f is constituted by a cylindrical body 3g and a free end having a conical profile 3h of which the wider base or flange 3h is provided to have an outer diameter greater than that of the body 3g. A slot 3i is machined in the middle of the finger 3f and over a part of its height to constitute two elastically deformable, parallel branches (FIG. 3).

The cylindrical body 3g is fixed in each ring 3a either by crimping or by screwing or the like. Finger 3f extends vertically and perpendicularly to the bearing surface 3b of each ring 3a.

The finger 3f is disposed near the conical bore 3d and the notch 3e.

An opening cylindrical hole 3j is provided in each of the rings 3a of the device 3. Hole 3j comprises near the bearing surface 3b an annular bead 3k. Opposite the bead, i.e. towards the spherical surface 3c, the hole 3j comprises a shoulder 3l whose inner diameter is substantially equivalent to that of the wider base of the conical profile 3h of finger 3f.

It will be noted that the finger 3f and hole 3j of each ring 3a are provided on either side of the conical bore 3d and near the notch 3e.

Device 3 may be used in conventional manner, i.e. the surgeon places a first ring 3a on all the pedicular screws 2 previously anchored. He then disposes the connecting rod 5 in the notch 3e of the first ring 3a before clipping the second thereon until the conical end 3h of each finger 3f cooperates with the shoulder 3l of the corresponding holes 3i. The surgeon then screws the nut 4 on the rod 2c of the pedicular screw 2 to immobilize the connecting rod 5 on the pedicular screws 2 and inside the devices 3, definitively.

When tightening the nut 4, it is ascertained that the conical part of the bore 3d of the ring 3a abuts against the spherical head 2b with a view to wedging thereon, making it possible, in combination with the connecting rod 5, to distribute the tightening forces in order to avoid rotating the pedicular screw 2 inside the pedicle 1a of the vertebra 1.

FIGS. 4 and 5 show the first position of the retaining device, which consists in introducing the fingers 3f inside the corresponding holes 3i of each ring 3a so that the latter can move freely with respect to one another. Each finger 3f is retained inside the corresponding hole 3j via the bead 3h. In this way, the surgeon prepares all the retaining devices 3 beforehand, so that the rings 3a are joined to one another but leaving a sufficient clearance for the passage of the connecting rod 5. After having screwed the pedicular screws 2 in the pedicles 1a of each vertebra 1, the surgeon positions all the previously prepared retaining devices 2 on each of the screws 2 and raises solely the upper ring 3a to position the connecting rod 5. The surgeon then proceeds to clip the rings 3a so that each conical part 3h of the fingers 3f cooperates with the shoulder 3l of the hole 3j. Device 3 and connecting rod 5 are definitively tightened with the aid of nut 4.

FIGS. 6 and 7 show the second position of use of the device 3, which consists in positioning a certain number of them on the connecting rod 5 before positioning the latter on the pedicular screws 2. In f act, the surgeon disposes all the devices 3 on the connecting rod 5 by clipping the rings 3a with respect to one another by means of the conical head 3h of each finger 3f inside the corresponding shoulders 3l.

It will be noted that the devices 3 may slide freely along the rod 5 so that the surgeon can dispose them opposite each pedicular screw 2 previously anchored in the pedicles 1a of the lumbar vertebrae 1. This latter position of the device 3 saves the surgeon a great deal of time and avoids his disposing fin the wound small-sized elements which might slip from his hands.

Definitive tightening of the connecting rod 5 is, of course, effected with the aid of the nut 4 which abuts on the spherical bearing surface 3c of the upper ring 3a. In fact, nut 4 comprises in its lower part a concave part with the same radius as that of the spherical part 3c of the rings 3a.

It must, moreover, be understood that the foregoing description has been given only by way of example and that it in no way limits the domain of the invention which would not be exceeded by replacing the details of execution described by any other equivalents.

What is claimed is:

1. Device for retaining a connecting rod of a spine fixator on pedicular screws previously anchored in the pedicles of the lumber vertebrae of a backbone, comprising two ring elements having opposing connecting rod engaging surface portions, each ring element including an elastically deformable retaining means which is receivable within a hole in the other of said ring elements said elastically deformable retaining means retaining said ring elements with respect to one another in different positions before the device is securely assembled on a pedicular screw.

2. The device of claim 1, wherein each ring element comprises a bore of conical profile for receiving a pedicular screw therethrough, and each said connecting rod engaging surface portion including at least one notch made perpendicularly to the bore.

3. The device of claim 2, wherein each ring element comprises a bearing surface and a spherical outer profile.

4. The device of claim 3, wherein said retaining means and said hole of each ring element are perpendicular to the bearing surface.

5. The device of claim 2, wherein said retaining means and said hole of each ring element are on opposite sides of said bore and adjacent said at least one notch.

6. The device of claim 2, wherein each of said retaining means comprises a cylindrical body of a first diameter and a free end with a conical profile which defines a flange having an outer second diameter greater than said first diameter, and a slot formed in said cylindrical body and said free end.

7. The device of claim 6, wherein each ring element includes a bearing surface, each hole including a bead disposed adjacent the bearing, surface and a shoulder of a diameter greater than said second diameter, said shoulder being spaced from said bead.

8. The device of claim 7, wherein each hole includes a portion between said bead and said shoulder which is smaller in diameter than said first diameter so as to create compression force on one of said retaining means inserted therein.

9. The device of claim 2, wherein each bore tapers outwardly towards a spherical outer profile of each ring element.

10. The device of claim 2, wherein said at least one notch of each ring element is semicircular and complimentary to a peripheral portion of a connecting rod.

11. The device of claim 2, wherein the bore of each ring element is configured so as to abut against a spherical part of a pedicular screw to thereby distribute tightening forces generated by a nut engaging each ring element when each ring element is connected to a pedicular screw and thereby resisting rotation of the pedicular screw inside a pedicle.

12. A device for retaining a connecting rod of a spine fixator on pedicular screws previously anchored in the pedicles of the lumbar vertebrae of a backbone, the device comprising, two clamping elements having opposing bearing surfaces and connecting rod engaging surface portions, each clamping element including a retaining means projecting therefrom and which is receivable within a hole in the other of said clamping elements, a bore through each clamping element for receiving a pedicular screw therethrough, each of said holes being of a configuration so as to cooperatively retain said clamping elements in a first position wherein said bearing surfaces are spaced relative to one another and a second position wherein said bearing surfaces are engaging one another, whereby said clamping elements are selectively maintained in different positions relative to another before being securely assembled on a pedicular screw.

13. The device of claim 12 in which each of said retaining means includes an elastically deformable element having a body portion and an outer end portion, said outer end portion including a flange having a diameter greater than a diameter of said body portion, and each of said holes including a first portion of a diameter to selectively receive said retaining means therein and a second portion of slightly greater diameter defining a shoulder of a size to cooperatively engage said flange of a retaining means inserted within said hole with said clamping element in said second position.

14. The device of claim 13 in which each of said holes includes an inwardly extending bead adjacent said bearing surfaces of said clamping elements, and each retaining means including a slot extending through said outer end portion and said body portion thereof.

* * * * *